United States Patent [19]
Aid

[11] Patent Number: 4,731,072
[45] Date of Patent: Mar. 15, 1988

[54] APPARATUS FOR HEATING OR COOLING FLUIDS

[75] Inventor: James D. Aid, St. Petersburg, Fla.

[73] Assignee: McNeilab, Inc., Fort Washington, Pa.

[21] Appl. No.: 394,582

[22] Filed: Jul. 2, 1982

Related U.S. Application Data

[62] Division of Ser. No. 262,162, May 11, 1981, abandoned.

[51] Int. Cl.⁴ .............................................. A61B 19/00
[52] U.S. Cl. .................................................. 604/408
[58] Field of Search .............. 126/426; 62/3; 604/403, 604/408 C, 410

[56] References Cited

U.S. PATENT DOCUMENTS

| | | | |
|---|---|---|---|
| 3,008,299 | 11/1961 | Sheckler | 62/3 |
| 3,022,781 | 2/1962 | Andrassy | 126/426 |
| 3,255,593 | 6/1966 | Newton | 62/3 |
| 4,059,095 | 11/1977 | Grundmann et al. | 126/426 X |
| 4,287,876 | 9/1981 | Jacques | 126/426 |

Primary Examiner—Lloyd L. King
Attorney, Agent, or Firm—L. Dennis Schuler

[57] ABSTRACT

Apparatus for heating or cooling fluids, particularly physiological fluids such as blood or plasma or fluids, such as dialysis fluid, which are used in the treatment of physiological fluids. Also disclosed are containers in which or through which fluids may be contained or circulated in order to effect heating or cooling.

21 Claims, 10 Drawing Figures

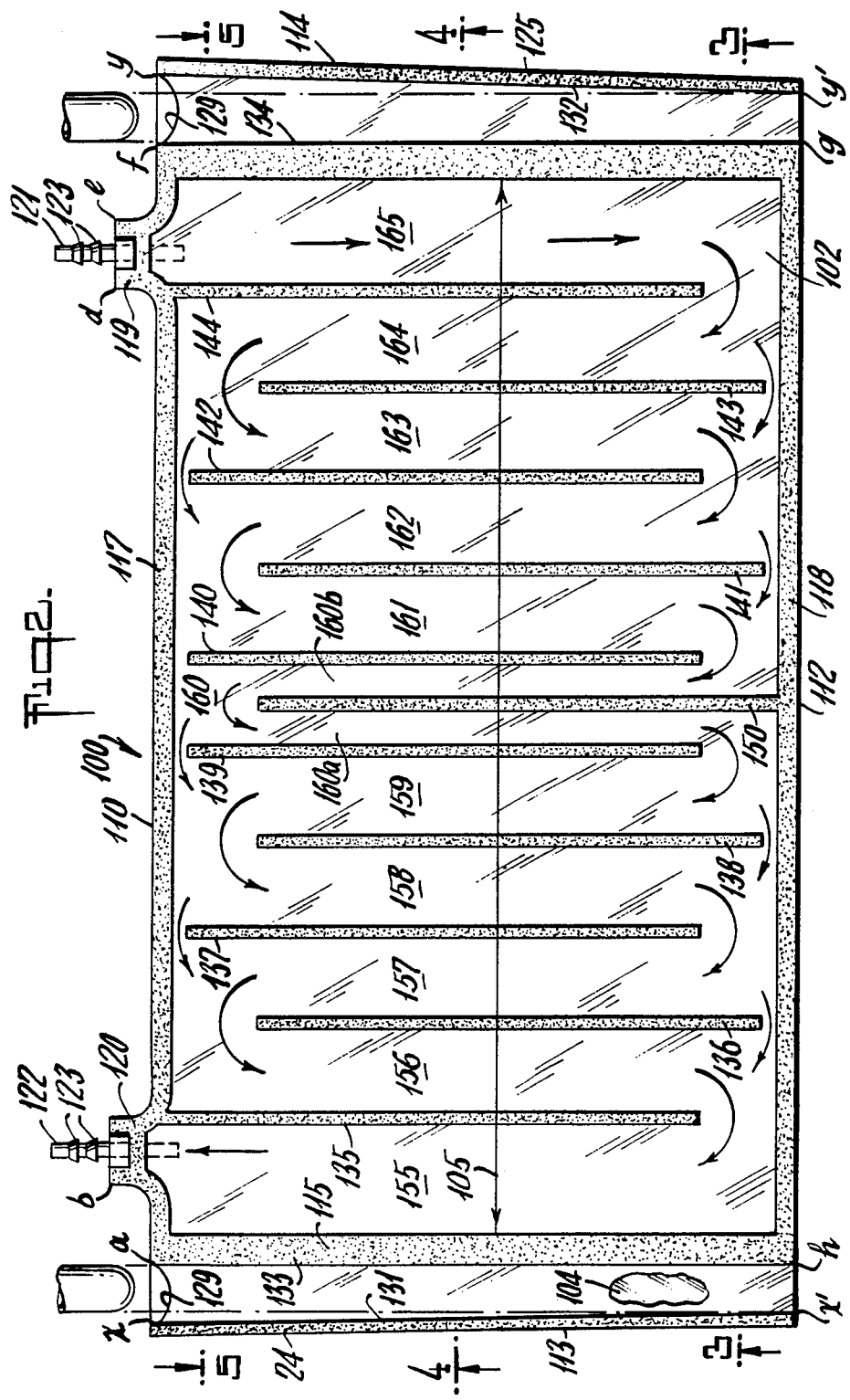

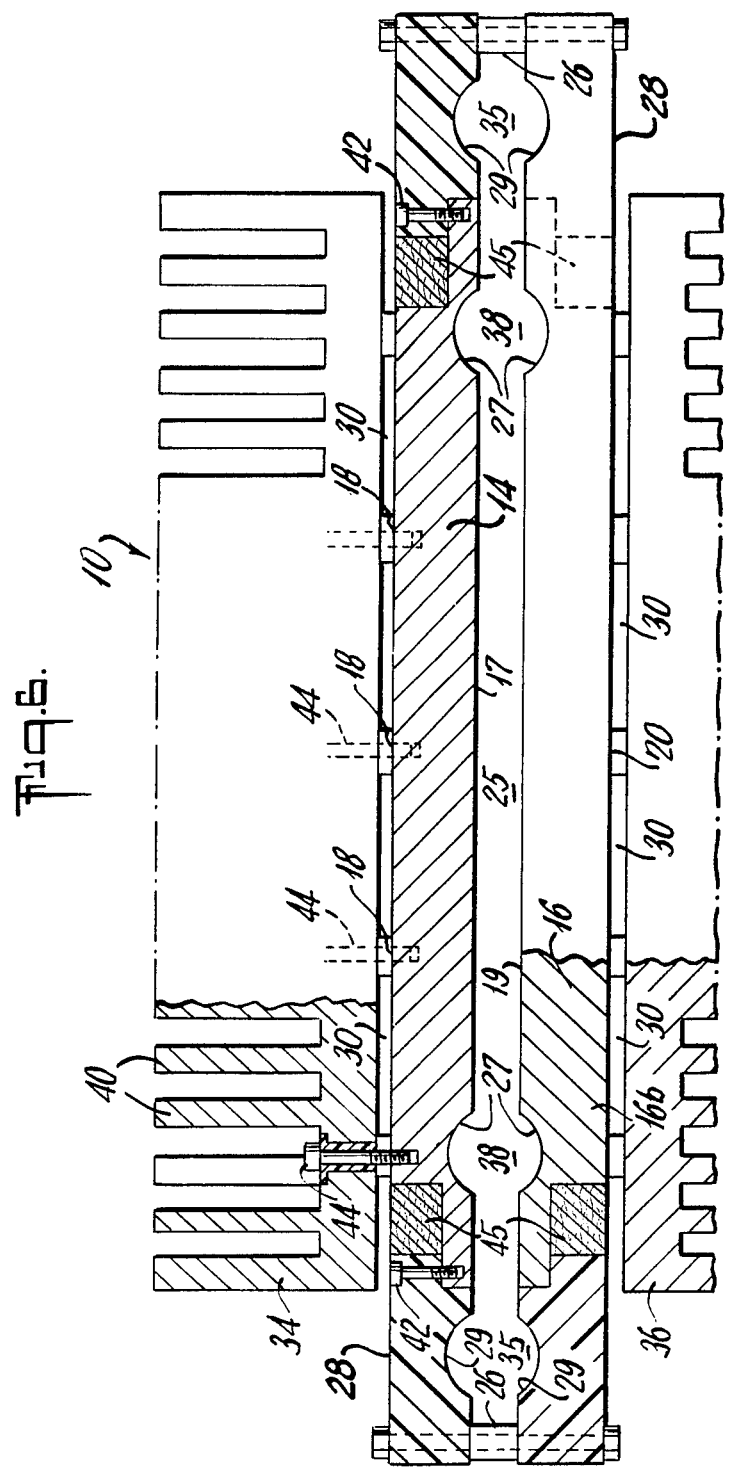

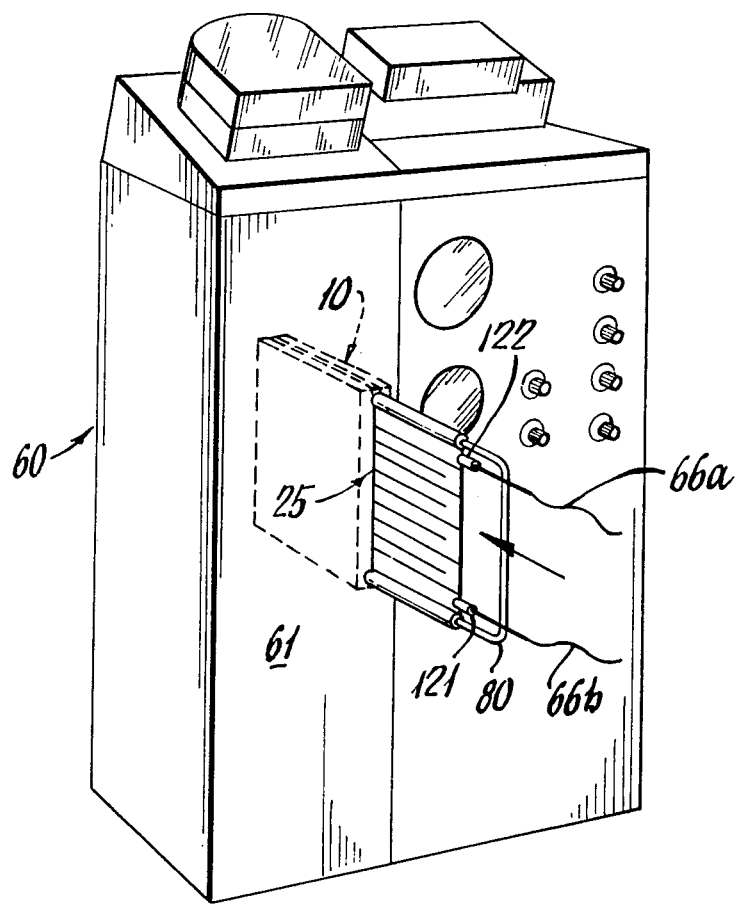

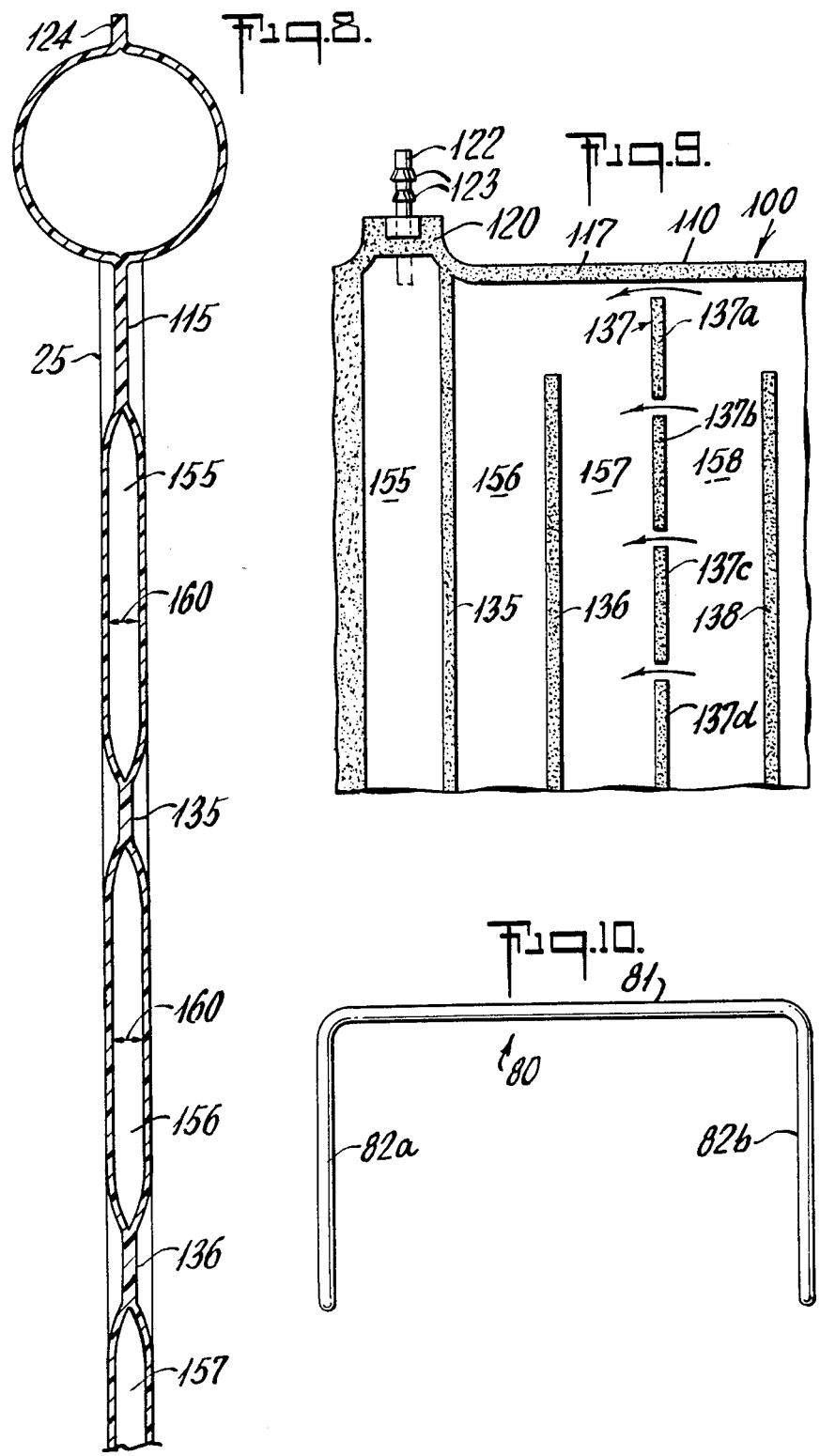

APPARATUS FOR HEATING OR COOLING FLUIDS

This is a division, of application Ser. No. 262,162, filed May 11, 1981, now abandoned.

BACKGROUND OF THE INVENTION

The present invention relates to apparatus for heating or cooling liquids. More particularly, it relates to apparatus for heating or cooling physiological fluids, such as whole blood and blood plasma, or liquids, such as dialysis fluid, which are used in the treatment of such physiological fluids. It also relates to containers in which or through which such fluids may be contained or circulated in order to affect heating or cooling.

It is frequently necessary or advisable during the course of medical treatment to heat or cool physiological fluids or to heat or cool liquids which are used in the treatment of such physiological fluids. For example, in haemodialysis it is common practice to heat the dialysis fluid before it enters the blood dialyzer. In heart-/lung bypass surgery employed a blood oxgenator, blood which has been oxygenated outside the body is generally rewarmed to about body temperature before being returned to the patient. In the collection of whole blood from donors, it is sometimes desirable to cool the collected blood prior to further processing. Similarly, in plasmapheresis, where blood is taken from a donor and separated by centrifugation or membrane filtration into a fraction comprising cellular components and a fraction comprising plasma, it is desirable to have heating apparatus or cooling apparatus available prior to further handling of the separated fractions. As an example, if the cellular component fraction is to be returned to the patient, either as such or with a specified volume of replacement fluid added thereto, it would be advantageous to warm same to approximately body temperature prior to such return. On the other hand, apparatus for cooling may be needed if the separated plasma fraction is to be subjected to further processing such as filtration or treatment with an absorbent substance. It will also be recognized that in some circumstances heating or cooling may be needed on a batch basis. Batch heating, for example, may be used in connection with the transfusion of blood; in that case, a bag of blood which has been refrigerated is usually warmed before the patient is transfused. In other circumstances, it may be necessary or desirable to effect heating or cooling on a continuous basis. In blood dialysis, for example, it is customary to heat the dialysate prior to passing it through the dialyzer. In plasmapheresis procedures, it may be desirable to cool either the separated cellular fraction or the separated plasma fraction on a continuous basis.

SUMMARY OF THE INVENTION

In accordance with one aspect of the present invention, there is provided apparatus which is adapted to receive a container means in which or through which a liquid to be heated or cooled is contained or circulated, said apparatus comprising a pair of thermally conductive elements, each of said elements having first and second thermally conductive major surfaces, said elements being arranged in spaced apart relationship with their respective first major surfaces facing each other so as to define therebetween a space for receiving said container, the second thermally conductive major surface of at least one of said elements having in contact therewith at least one thermoelectric device for heating or cooling, said at least one thermoelectric device being in contact with heat sink means.

Preferably, the second thermally conductive major surface of each of the thermally conductive elements has at least one thermoelectric device in contact therewith and each of the thermoelectric devices is in contact with a heat sink means.

In accordance with another aspect of the present invention, apparatus for heating or cooling liquids includes a container means for holding a liquid to be heated or cooled, and a pair of thermally cnductive elements, each of said elements comprising first and second thermally conductive major surfaces. The pair of thermally conductive elements are arranged in spaced apart relationship with their respective first thermally conductive major surfaces facing each other so as to define therebetween a space for receiving said container means. The second thermally conductive major surface of each thermally conductive element has at least one thermoelectric device for heating or cooling in contact therewith. The remote surface of this thermoelectric device (that is, the surface thereof which is not in contact with the thermally conductive element) is in contact with a heat sink means. A substantial portion of the space surrounding the thermoelectric device and located generally between the second major surface of the thermally conductive element and the heat sink is preferably filled with an insulation material.

In accordance with still another aspect of the present invention, there is provided a generally flexible container means which is adapted to be removably secured to a frame means. The flexible container means and its accompanying frame member are sized so they can readily be inserted into the aforementioned space defined by the spaced pair of heat conducting elements. The frame member is generally U-shaped and comprises a pair of substantially parallel arm members joined by a cross member. The container means, which is in the form of a flat bag whose two major walls comprise relatively thin, generally flexible sheets of a polymeric material, has a pair of tapered, laterally extending, pockets or sleeves for receiving the arms of the frame member. The bag and frame member are sized and constructed so that when the arms of the frame member are inserted into the pockets of the bag, the leading edge of the bag, that is, the edge of the bag which runs perpendicularly to the arms of the frame and which is farther from the cross member thereof, is tensioned therebetween. The tensioning serves to straighten out the leading edge of the bag, thus facilitating, for example, the insertion of the bag and frame combination into the space defined by the thermally conductive elements of the aforementioned apparatus for heating and cooling. In a preferred embodiment, the container means further includes a plurality of internal channels having substantially identical widths and which serve to direct the flow of liquid through the bag in alternating directions. In an even more preferred embodiment, one of the aforementioned channels is subdivided into two secondary channels of reduced width.

The foregoing and other features of the present invention will be described in greater detail with reference to the accompanying drawings. While the apparatus of the present invention is described herein with reference to the heating or cooling of physiological fluids or with reference to the heating or cooling of liquids which are used to treat such physiological fluids, it will be apparent to those skilled in the art that the apparatus may also be used to heat or cool other types of liquids.

BRIEF DESCRIPTION OF THE DRAWINGS

FIG. 2 is a perspective view of a preferred embodiment of a container means of the present invention and which can be employed in the apparatus of the present invention.

FIG. 6 is a top view, with some parts in cross-section, other parts enlarged, and still other parts cut away, of an apparatus in accordance with the present invention.

FIG. 7 is a perspective view showing the container means of the present invention being inserted into a cabinet which includes the apparatus of FIG. 6.

FIG. 8 is a partial view, greatly enlarged and partially in cross-section, of the container means positioned in the apparatus of FIG. 6.

FIG. 9 is a partial view of an alternate embodiment of the container means of the present invention.

FIG. 10 is a plan view of a U-shaped frame member for the container means of the present invention.

DESCRIPTION OF THE PREFERRED EMBODIMENT

Figure 1:
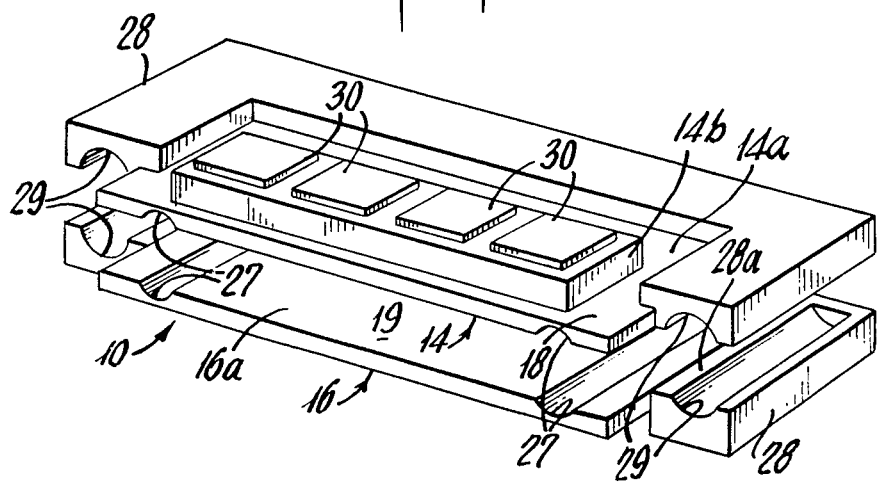
FIG. 1 is a partial perspective view of the arrangement of the thermally conductive elements and thermoelectric devices for heating and cooling used in one embodiment of the apparatus of the present invention.
Figure 4:
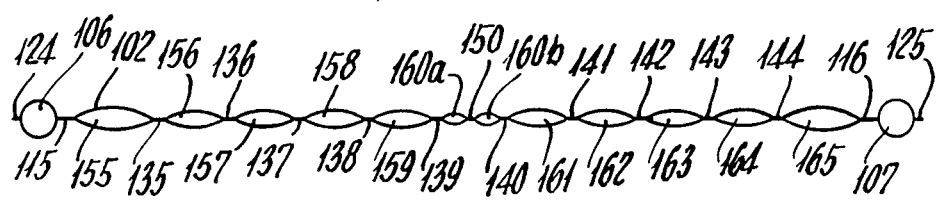
FIG. 4 is a cross-sectional view taken along line 4—4 of FIG. 2.
Figure 3:
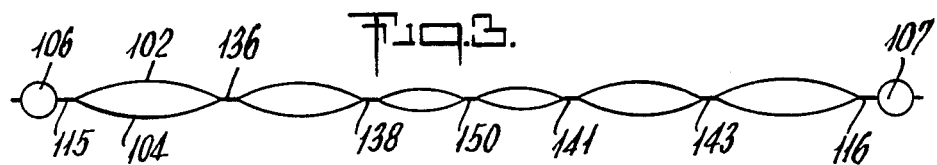
FIG. 3 is a cross-sectional view taken along line 3—3 of FIG. 2.
Figure 5:
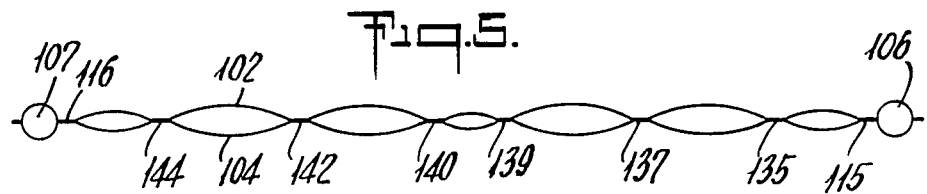
FIG. 5 is a cross-sectional view taken along line 5—5 of FIG. 2.

Referring now to FIGS. 1 and 6 of the drawings, there is shown a preferred embodiment of the apparatus adapted to receive a container means in which or through which a liquid to be heated or cooled is contained or circulated. Apparatus 10 comprises a pair of substantially identical thermally conductive elements 14, 16. Thermally conductive element 14 has a first thermally conductive major surface 17 and a second thermally conductive major surface 18. Correspondingly, thermally conductive element 16 has a first thermally conductive major surface 19 and a second thermally conductive major surface 20. Thermally conductive elements 14, 16 have base portions 14a and 16a, respectively, as well as elevated portions 14b and 16b, respectively, the elevated portions having smaller areas than the base portions. Elements 14, 16 are conveniently machined from suitably sized pieces of aluminum, but it will be recognized that other conductive materials may be used for this purpose. In addition, it will be understood that the elevated portions and base portions may be made separately and subsequently fastened together, for example with screws. Thermally conductive elements 14, 16 are arranged in the apparatus in a spaced apart relationship such that their respective first thermally conductive major surfaces 17, 19 face each other so as to define therebetween a space 25 for receiving a container means in which heating or cooling may be effected. Elements 14, 16 are maintained in their desired spaced apart relationship by the use of spacer 26. A rabbet molding 28, preferably made of a non-heat-conductive material such as polyvinyl chloride, surrounds the periphery of base portions 14a and 16a so as to leave the first thermally conductive major surfaces copletely free of any molding. Thus, referring to FIG. 1, first thermally conductive major surface 19 of thermally conductive element 16 and surface 28a of molding 28 are in the same plane.

Each of heat conducting elements 14, 16 has at least one thermoelectric device 30 for heating or cooling secured to its second major heat conducting surface. Such thermoelectric devices are commerically available from several companies in the U.S. and may be obtained in a range of wattage ratings for use with various direct current voltages. These devices have a pair of electrical lead wires for connection to the source of direct current. One electrical polarity allows the thermoelectric device to provide a cooling effect while the opposite electrical polarity allows the device to provide a heating effect.

In the preferred embodiment, four thermoelectric devices 30 rated at thirty watts were secured to each heat conducting element 14, 16 so that space 25, and the container means and fluid contained or flowing therein, could be heated to a temperature of about 38° C. or cooled to a temperature of about 2° C. The specific number of thermoelectric devices to be employed with any given apparatus depends on a variety of factors, among them the size and capacity of the device itself, the size of the thermally conductive elements, the volume of space 25, and the temperature range intended for that space. In one specific embodiment of apparatus according to the present invention, the thermally conductive elements 14, 16 were machined from pieces of aluminum plate. Base portions 14a and 16a were 10 inches (25.4 cm.) long, 5 inches (12.7 cm.) wide, and ¼ inch (0.635 cm.) thick. Elevated portions 14b and 16b were about 8 inches (20.3 cm.) long, 2 inches (5.1 cm.) wide and ½ inch (1.27 cm.) thick. Thermoelectric devices 30 measured about 1½ inches (3.81 cm.) square by ⅛ inch (0.318 cm.) thick. As illustrated in FIG. 1, four of the thermoelectric devices 30 were secured to the remote surface of elevated portion 14b. Thus thermoelectric devices 30 were brought into heat-conducting contact with the second thermally conductive major surface 18 of thermally conductive element 16. Four thermoelectric devices 30 were secured to the remote surface of elevated portion 16b thus bringing those devices into heat-conducting contact with the second thermally conductive major surface 20 of thermally coductive element 16.

Apparatus 10 further comprises a pair of heat sinks 34 and 36. In the preferred embodiment under discussion, the heat sinks have the same length and width as base portions 14a and 16a, and are about 2 inches (5.1 cm.) thick. The heat sinks, whose function is to remove heat in the cooling mode and cold in the heating mode, can be made of extruded aluminum. Preferably, the heat sinks comprise fins 40 to increase their efficiency.

Apparatus 10 also may advantageously include insulation material 45 which may, for example, be a closed cell polyurethane or polyester foam. Other insulative materials may be used. The insulation has about the same thickness as that of elevated portions 14b and 16b and covers those regions of the second thermally conductive major surfaces of base portions 14a and 16a which are not contacted by either their respective elevated portions 14b, 16b, or molding 28. In the preferred embodiment being discussed, molding 28 extends inwardly about ¼ inch (0.635 cm.) from the peripheral edges of elements 14 and 16. Thus the insulation used in the preferred embodiment would be in the form of a rectangle measuring about 9½ inches (24.1 cm.) long, 4½ inches (11.43 cm.) wide, and ½ inch (1.27 cm.) thick and having an interiorly located opening of about 8 inches (20.3 cm.) long and 2 inches (5.1 cm.) wide. It will be noted that the thickness of the insulation is substantially the same as the thickness of elevated portions 14b and 16b while the dimensions of the interiorly located opening therein is substantially the same as the outer dimensions of those elevated portions.

As shown in FIG. 6, elements 14 and 16 preferably have arcuate cutout portions 27 located in their first thermally conductive major surface 17 and 19, respectively. These cutout portions are located near each end of the elements 14, 16. In addition, molding 28 has a pair of cutout portions 29. It will be recognized that certain portions of FIG. 6 have, for purposes of clarity, been illustrated in larger than actual size. For example, space 25 in an actual embodiment of apparatus 10 can conveniently be about 60 mils wide and arcuate portions 27 and 29 can conveniently have a diameter of about ⅜ inch (0.95 cm.). It will be understood that space 25, arcuate cutout portions 27 and arcuate cutout portions 29 are adapted to receive the frame and container means combination shown in FIG. 2. Arcuate cut-out poritions 29 at either end of the apparatus, along with space 25 therebetween, define a pair of generally circular openings 35 which are adapted to receive the opposed arms of the frame element. Cut-out portions 29 extend for nearly the entire length of the side portions of molding 28. The two cutout portions 27, along with space 25 therebetween define another pair of circular openings 36 which, when the frame and container means combination is fully inserted into space 25, are adapted to receive the inlet and outlet of the container means. Since, as will be seen hereinafter, the inlet and outlet have a short length, arcuate cut-out portions 27 need by cut only a short distance into elements 14, 16.

Referring to FIG. 7, there is shown a perspective view of a cabinet 60 which comprises, in addition to other components, apparatus 10 for heating or cooling. In this view, the entrance to space 25 of apparatus 10 is located substantially flush with the front panel 61 of the cabinet. The frame and container combination is shown in the process of being inserted, from front to back of the cabinet, into space 25. A portion of container means 100 adjacent its bottom edge 112 (which is not visible in FIG. 7) has been tensioned between rigid arms 82a, 82b of frame 80. As a result, the leading edge of the container/frame combination has been straightened, thus facilitating insertion of the combination into space 25. Thus apparatus 10 has been made a permanent component in cabinet 61. The container means, being relatively inexpensive to construct, is preferably disposed of after a single use. The frame member can be disposable, in which case the frame/container combination would be supplied as a unit from the manufacturer or it can be adapted for multiple use. In the former event, the frame could be constructed of a rigid plastic; in the latter case, the frame is conveniently made from 5/16" steel rod or equivalent material.

Apparatus 10 advantageously may include a fan means (not illustrated in the accompanying drawings) for blowing air across heat sinks 34 and 36.

The assembly of apparatus 10 can be understood with reference to FIG. 6. Elements 14 and 16, as indicated earlier, are machined to the desired dimensions from single pieces of aluminum plate. Arcuate surfaces 27 are provided in the first thermally conductive surface of each element. Thermoelectric devices are positioned on the elevated portions 14b and 16b. If desired, a commerically available, thermally conductive grease may be placed between the lower surfaces of the thermoelectric devices and the upper surfaces of the elevated portions. Molding 28, with arcuate cutout portions 29 in the side portions thereof, is placed around elements 14, 16 as illustrated in FIG. 1 and secured to their peripheries with screws 42. Insulation 45 is put into place and the heat sinks are fastened to the thermally conductive elements by a series by screws 44, three of these screws being placed adjacent thermoelectric devices 30. When screws 44 are tightened, the thermoelectric devices are "sandwiched" between the heat sinks and the thermally conductive elements, assuring the necessary thermally conductive contact. The first thermally conductive major surfaces of elements 14, 16 are separated by a spacer 26 which has a thickness corresponding to the width desired for space 25. The device is bolted together with a series of nuts and bolts 26 passing through molding 28.

The electrical leads from the thermoelectric devices are connected in the desired polarity to a source of D.C. voltage. If it is desired to heat or cool at one's option, appropriate switch means are used in the electrical connections so that when the switch is in one position the proper polarity for cooling is provided and when the switch is in the other position, the proper polarity for heating is provided.

The container means of the present invention is in the form of a generally flat bag whose two major walls comprising relatively thin, generally flexible sheets plastic material, such as polyethylene, polypropylene, polyvinyl chloride, poly(ethylene-vinyl acetate), nylon or the like, which are secured together in the manner explained hereinafter. The container means comprises a generally centrally located compartment for containing a liquid, and a pair of elongated tapered pockets or sleeves, one said sleeve adjoining each side edge of that compartment, through which, as will be seen, the substantially parallel arms of a frame element may be inserted. The container comprises an inlet means for introducing a liquid into the compartment and an outlet means for withdrawing a liquid from the compartment.

The compartment for containing a liquid preferably includes means for directing the flow of that liquid back and forth within the compartment. These flow directing means, which subdivide the compartment into a plurality of primary channels for the flow of liquid, preferably comprise a plurality of interiorly located attachment lines within the aforementioned compartment. As used herein, the term "attachment line" or "line of attachment" refers to a line along which the two sheets of plastic comprising the container means are secured together, for example, by heat sealing, gluing, or ultrasonic welding, heat sealing being preferred. Individual attachment lines of a first plurality are alternated with individual attachment lines of a second plurality so as to form a series of parallel channels through which a liquid can flow in a back-and-forth pattern.

Each of the pockets or sleeves comprising the container means has an inner edge, which is adjacent the side edge of the compartment for containing a liquid, and an outer edge, which is near, or coincides with, the side edge of the container means. A feature of the container means of the present invention is that its sleeves or pockets are tapered, that is, each pocket is wider at one end of the container means than it is at the other. The tapered pockets have two advantages. The first advantage is that the wider ends of the pockets make it easy to insert the opposed arms of a frame element. The second advantage is that, as the arms of the frame element are inserted further and further into the pockets, the portion of the container means between the narrower portions of the pockets becomes tensioned between the arms of the frame element. This tensioning provides a substantially straightened leading edge so that the bag and frame combination can be easily inserted into a narrow receiving slot such as space 25 of the earlier described apparatus for heating or cooling.

A preferred embodiment of the container means of the present invention is constructed from two substantially identical pieces or sheets 102, 104 of polyethylene plastic having a thickness of 5 mils. Each sheet 102, 104 of plastic has a top edge, an opposed bottom edge, a pair of opposed side edges connecting the ends of the top and bottom edges, and a pair of apron-like tabs projecting from the upper edge near each of the side edges. The two sheets of plastic are aligned and are then heat-sealed to each other along relatively narrow lines or bands of attachment to provide container means 100 comprising a compartment 105 for holding liquid and a pair of narrow sleeves or pockets 106, 107. For clarity, the lines or bands of attachment along which the two plastic sheets are attached to each other are shown in FIG. 2 as stippled lines. Heat sealing along vertical lines of attachment 115, 116 provides liquid tight sides for compartment 105, while heat sealing along horizontal line of attachment 118 provides a liquid tight bottom for the compartment. Except for the presence of inlet 121 and outlet 122 (both discussed hereinafter), heat sealing along horizontal line of attachment 117 (which includes the apron-like projection 119, 120 mentioned below) provides a liquid-tight top for the compartment.

As seen in FIG. 2, sheets 102 and 104 are additionally heat sealed along lines of attachment 124, 125 at side edges 113, 114 respectively of container means 100. Heat sealed regions 124 and 115 define the sides of one pocket or sleeve 106 at one side of the container and heat sealed regions 125 and 116 define the sides of a second pocket or sleeve 107 at the opposite side of the container. As shown in FIG. 2, in the preferred embodiment, pockets 106, 107 are open at both their ends and semicircular portions of plastic have been cut out of plastic sheet 102 to provide a notched portion 129 at the top of each sleeve or pocket. It will be recognized that heat seal line 118 can be extended at its ends until it meets the lower ends of heat seal lines 124, 125 if it is desired to provide closed ends for pockets 126, 127.

Upon completion of the heat sealing, there is provided container means 100 having a top edge 110, an opposed bottom edge 112, a pair of opposed side edges 113, 114, and two apron-like tabs 119, 120. Tab 119 surrounds an inlet means 121 for introducing a liquid into compartment 105; similarly tab 120 surrounds an outlet means 122 for withdrawing a liquid from compartment 105. Inlet 121 and outlet 122 are made of short lengths of polyethylene tubing having an inside diameter of about 0.12 inch (0.3 cm.) and an outside diameter of about 0.16 inch (0.4 cm.). The inlet and outlet preferably extend a short distance into compartment 105 and may have ridge portions 123 in order to provide a firmer grasp on tubing connected thereto. There must, of course, be a liquid tight seal at the inlet and outlet. This is accomplished in the preferred embodiment under discussion by heat sealing the apron-like tabs of sheets 102, 104 to each other and to the inlet and outlet tubes during the assembly operation. Alternatively, or as an adjunct to heat sealing, any suitable adhesive may be applied to the outer surfaces of the inlet and outlet in order to insure the necessary liquid tight seal. Thus, the heat sealing steps described above provide and define compartment 105 for holding liquid, the periphery of said compartment being designated by the letters a, b, c, d, e, f, g, and h in FIG. 2.

As indicated earlier herein, pockets 106, 107 are provided at the sides of container means 100 in order to receive the arms of a frame element 80, illustrated in FIG. 10. This frame element, which in its simplest form is U-shaped and may be made of, e.g., 5/16 inch steel rod bent into the required shape, comprises a cross member 81 and a pair of opposed, substantially parallel arms 82a, 82b. Pockets 106, 107 are tapered, that is, their width is greater at the top of the container means than their width at the bottom. Referring to FIG. 2, it will be seen that the outer edge 131 of pocket 106 coincides with and is defined by the inner edge of heat seal line 124; in the same way, the outer edge 132 of pocket 107 coincides with and is defined by the inner edge of heat seal line 125. In order to achieve the advantages of the present invention, pockets 106 and 107 must have inwardly tapered outside edges 131 and 132 respectively. Stated alternatively, the desired tapered pockets are characterized by the fact that the straight-line distance, measured along top edge 110 from point x to point y, between outer edge 131 of pocket 106 and outer edge 132 of pocket 107 is greater than the straight-line distance, measured along lower edge 112 from point x' to point y', between outer edge 131 of pocket 106 and outer edge 132 of pocket 107.

Where container means 100 is to have a liquid flowing through it, for example, when the liquid is to be heated or cooled on a continuous basis, it is preferred in order to increase efficiency and minimize shunting to provide means for directing the liquid to flow back and forth in compartment 105. These flow directing means preferably comprise a plurality of lines or bands of attachment 135-144 located interiorly of sides 115, 116 of compartment 105 and which define a plurality of primary channels 155-164 through which the liquid can flow. The lines of attachment can be formed by any of the aforementioned methods of gluing, ultrasonic welding or heat sealing, the latter method being preferred. Lines of attachment 135-144 must be wide enough to retain their integrity when the container has a liquid in it. Making the lines of attachment wider than needed for the purpose of strength and integrity merely results in an undesirable and unnecessary reduction in the liquid holding capacity of compartment 105. It has been found that a width of ⅛ inch (0.32 cm.) is suitable for lines of attachment 135-144. In the preferred embodiment under discussion, lines of attachment 135-144 all have a width of ⅛ inch (0.32 cm.) and are evenly spaced on a center-to-center basis within compartment 105 to provide a plurality of primary channels 156-164 for the flow of liquid. Each of channels 156-164 has substantially the same width which, in the embodiment under discussion, is about ¾ inch (1.9 cm.). Channel 155 (defined by lines of attachment 115 and 135) and channel 165 (defined by lines of attachment 116 and 144) are somewhat wider than channels 156-164; specifically, in the preferred embodiment channels 155 and 165 are about one inch (2.54 cm.) wide. It will be recognized that channels 155 and 156 need not be wider than channels 156–164; they could also have the same width or be narrower.

The lines of attachment 135–144 have a length which is greater than 50% of the distance between the top and bottom edges of the container; preferably, their length is more than 80% of this top-to-bottom distance.

In order to prevent undesirable shunting of liquid at inlet 121 and at outlet 122, it is necessary that the interiorly located line of attachment nearest the inlet and the interiorly located line of attachment nearest the outlet form a liquid tight junction at that end edge of the container means where the inlet and outlet are located. Thus, in the embodiment of FIG. 2, line of attachment 144 forms a liquid tight junction with horizontal line of attachment 117 just interiorly of the point where inlet 121 is located at the top of the container means, and line of attachment 135 forms a liquid tight junction, also with horizontal line of attachment 117, just interiorly of the point where outlet 122 is located.

It will be noted that lines of attachment 136, 138, 141, and 143 are placed somewhat closer to bottom heat seal line 118 than to top heat seal line 117, whereas lines of attachment 137, 139, 140, and 142 are placed somewhat closer to top heat seal line 117 than to bottom heat seal line 118. Although not illustrated in FIG. 2, the ends of lines 136, 138, 141, and 143 can be extended so they form a liquid tight junction with heat seal line 118, and the ends of lines 137, 139, 140, and 142 can be extended so they form a liquid tight junction with heat seal line 117. When the lines are so extended, liquid must flow to the end of one liquid flow channel before entering the next adjacent liquid flow channel. With the arrangement shown in FIG. 2, where lines 136, 138, 141, and 143 are spaced about 3/32" (0.24 cm.) from the edge of heat seal line 118 and lines 137, 139, 140, and 142 are spaced the same distance from heat seal region 117, the liquid flows primarily downwardly in one channel and upwardly in the next adjacent channel. In addition, there are secondary flow paths available where the lower ends of lines of attachment 136, 138, 141, and 143 are spaced from heat seal line 118 and where the upper ends of lines of attachment 137, 139, 140 and 142 are spaced from heat seal line 117. In FIG. 2, the wider arrows indicate primary liquid flow paths, and narrower arrows indicate secondary flow paths. This arrangement of the lines of attachment to provide for primary and secondary flow paths is particularly advantageous, e.g. when blood is flowing through the bag, because it minimizes regions in which the blood may stagnate.

In accordance with another feature of the present invention, one of the primary flow channels defined by a selected pair of interiorly located lines of attachment is reduced in width by interposing therebetween an additional line of attachment. This additional line of attachment must be joined to either the top or bottom edge of the container means to form a liquid tight junction. As illustrated in FIG. 2, an additional line of attachment 150 is placed between lines of attachment 139 and 140. Line 150 is extended into heat seal line 118 at the bottom of the bag to form a liquid tight junction at that point. It will be appreciated that liquid flow channel 160 defined by lines of attachment 139, 140 is, by the interposition of the additional line of attachment 150, divided for nearly its entire length into two secondary liquid flow channels, 160a, 160b of reduced width. Container means 100 then has eight primary flow channels (156, 157, 158, 159, 161, 162, 163 and 164) of substantially equal width, two flow channels (155 and 165) of slighty larger width, and two secondary flow channels (160a, 160b) of reduced width. With this arrangement, the rate of flow of liquid through the narrower, secondary channels 160a, 160b is substantially greater than the rate of flow through the wider, primary channels. This increase in the rate of flow in the narrower channels is advantageous because it provides better liquid mixing and tends to increase the efficiency of the heating or cooling operation. As shown in FIG. 2, the two narrower channels formed by the interposition of line of attachment 150 are preferably located centrally of compartment 105.

Where only one pair of narrower, secondary flow channels is to be provided in the container means, it is preferred, as shown in FIG. 2, that the line of attachment (i.e., line 150) which subdivides the primary channel (i.e., channel 160) be located generally centrally of compartment 105. It is also possible to provide additional secondary flow channels where for example there are to be two pairs of narrower, secondary flow channels, it is preferred that the two subdividing lines and its nearer side edge of compartment 105 is equal to the distance between the other of the subdividing lines and its nearer side edge of compartment 105. For example, one of the subdividing lines of attachment can be located between lines of attachment 137 and 138 so as to subdivide primary channel 158 into a first pair of secondary channels and the other of the sub-dividing lines of attachment can be located between lines of attachment 141 and 142 so as to subdivide primary channel 162 into a second pair of secondary channels. When thus constructed, container means 100 has seven primary flow channels (156, 157, 159, 160, 161, 163 and 164) of substantially equal width, two flow channels (155 and 165) of somewhat larger width, and two separated pairs of secondary flow channels which, although not specifically labelled as such in the drawings, would be designated 158a, 158b and 162a, 162b.

FIG. 8 is a partial cross-sectional view, greatly enlarged, showing container means 100 in its position in space 25 of apparatus 10. The container is illustrated in the configuration which it assumes when placed in space 25 and with a liquid in it. The degree to which compartment 105 of the container expands due to the force of the liquid therein is restricted and effectively controlled by the width of space 25, which in the preferred embodiment described earlier herein is 60 mils. Thus it will be seen that the flow channels, typified in FIG. 8 by channels 155 and 156, have assumed a rectangular shape with more or less rounded end portions.

If, as described earlier herein, container means 100 is constructed of 5 mil thick sheets of plastic and space 25 measures 60 mils, then the maximum thickness 160 of the liquid flow channels is about 50 mils. The foregoing dimension allow for acceptable priming volumes and for efficient heat transfer to or from the liquid in the container at liquid flow rates of up to 200 cc. per minute. Those skilled in the art will recognize that if the liquid flow rate is kept constant and the effective, thickness 160 is reduced, the priming volume will be reduced, heat transfer efficiency will increase, and the turbulence of the flow will increase. While reduced priming volume and increased heat transfer efficiency would be advantageous, increased turbulence might not be desirable or acceptable as, for example, where blood is being heated or cooled. On the other hand, if the system must handle higher flow rates, it will probably be necessary, if it is desired to avoid turbulence, to increase thickness 160 and accept whatever increase in priming volume and reduction in heat transfer efficiency accompanies that increase.

Referring now to FIG. 9, there is shown an alternative construction wherein line of attachment 136 comprises a plurality of smaller lines of attachment 137a, 137b, 137c, and 137d having small gaps therebetween. Such a construction can be used where it is desired to provide secondary flow paths between adjoining channels.

The container means of the present invention can, if desired, to provide with two lengths of tubing, 66a, 66b one being connected to inlet 121 and the other to outlet 122 (see FIG. 7). The unconnected ends of these lengths of tubing may carry cubing connectors for connecting inlet 121 to a source of liquid and for connecting outlet 122 so that the liquid may be sent to additional pieces of equipment for further processing or, if appropriate, returned to the patient.

If container means 100 is intended for use with body fluids, such as blood or plasma, which must not be contaminated, than those portions of the container means (and tubing, connectors, etc. which may be associated therewith) must be made from non-contaminating, body fluid compatible raw materials.

What is claimed is:

1. A flexible container means adapted to be received in a frame means having a cross member from which extends a pair of substantially parallel arm elements and in which a liquid may be stored or through which a liquid may be circulated, said container means comprising a pair of walls including two relatively thin, generally flexible sheets of a polymeric material, a top edge, a bottom edge, a centrally located compartment for containing said liquid, an elongated sleeve adjoining each side edge of said compartment, an inlet for introducing said liquid into said compartment and an outlet for withdrawing said liquid from said compartment, each of said sleeves having an inner edge and an outer edge, the straight-line distance between the outer edges of said sleeves being greater along the top edge of the container means than the straight-line distance between the outer edges of said sleeves along the bottom edge of said container means.

2. Container means according to claim 1 in which the inlet means and the outlet means are located along the top edge of the container means.

3. Container means according to claim 1 in which the inlet means is located along said top edge near one of the side edges of said compartment and said outlet means is located along said top edge near the other of the side edges of said compartment.

4. Container means according to claim 3 in which said elongated sleeves are coextensive with the side edges of said compartment.

5. Container means according to claim 1 further including means associated with said compartment for dividing said compartment into a plurality of channels for the flow of liquid therethrough.

6. Container means according to claim 5 in which said plurality of channels have substantially identical widths.

7. Container means according to claim 6 further including means for dividing at least one of said plurality of channels into two narrower channels of substantially identical widths.

8. Container means according to claim 6 further including means for dividing one of said plurality of channels into two narrower channels of substantially identical width.

9. Container means according to claim 1 in which said two sheets of polymeric material comprising the walls of said container are joined to each other along relatively narrow, substantially equally spaced lines of attachment located interiorly of said compartment whereby a plurality of channels for the flow of liquid is provided in said compartment.

10. Container means according to claim 9 in which said channels have substantially identical widths.

11. Container means according to claim 10 in which said two sheets of polymeric material comprising the walls of said container are joined to each other along at least one additional interiorly located line of attachment so as to divide at least one of said plurality of channels into two narrower channels of substantially identical width.

12. Container means according to claim 10 in which said two sheets of polymeric material comprising the walls of said container are joined together along one additional interiorly located line of attachment so as to divide one of said plurality of channels into two narrower channels of substantially identical width.

13. Container means according to any one of claims 9 through 12 wherein said lines of attachment are parallel to the sides of said container and said inlet means and said outlet means are located along the top edge of said container.

14. Container means having a top edge, a bottom edge, a pair of opposed side edges, a pair of walls including two relatively thin, generally flexible sheets of a polymeric material, an inlet for introducing a liquid into said container means, an outlet for withdrawing a liquid from said container means, said sheets of material being joined to each other along at least two relatively narrow, internally located lines of attachment to form within said container means at least three primary channels of substantially equal width, said sheets of material being further joined together along at least one additional line of attachment to subdivide at least one of said three primary channels into two secondary channels of reduced width, the number of secondary channels means never being more than the number of primary channels.

15. Container means according to claim 14 wherein said lines of attachment are parallel to said pair of opposed side edges.

16. Container means according to claim 15 wherein said inlet means and said outlet means are located along said top edge.

17. Container means according to claim 16 wherein the line of attachment immediately adjacent one of said side edges forms a liquid-tight seal with the top edge of said container means and said inlet means is located along said top edge between said one of said side edges and said line of attachment immediately adjacent said one of said side edges.

18. Container means according to claim 17 wherein the line of attachment immediately adjacent the other of said side edges forms a liquid-tight seal with the top edge of said container means and said outlet means is located along said top edge between said other of said side edges and said line of attachment immediately adjacent said other of said side edges.

19. Container means according to claim 18 wherein said additional line of attachment forms a liquid-tight seal with one of said top and bottom edges of said container means.

20. Container means according to claim 19 wherein said additional line of attachment forms a liquid-tight seal with the bottom edge of said container.

21. Container means according to claim 20 having ten channels of relatively wider, substantially equal width and two channels of relatively narrower width.

* * * * *